United States Patent [19]

Schrier

[11] Patent Number: 5,362,425
[45] Date of Patent: Nov. 8, 1994

[54] ORGANIC OIL SPRAY-DRYING TECHNIQUES

[75] Inventor: Bruce K. Schrier, Wooster, Ohio

[73] Assignee: Technology Unlimited, Inc., Wooster, Ohio

[21] Appl. No.: 964,894

[22] Filed: Oct. 22, 1992

[51] Int. Cl.$^5$ ............ B01J 13/04; A01N 25/28; A23L 2/26

[52] U.S. Cl. .................... 264/4.6; 264/4.1; 424/408; 424/418; 424/493; 426/98; 426/103; 426/534; 428/402.2; 512/4

[58] Field of Search ............ 264/4.1, 4.6; 428/402.2; 424/408, 418, 493; 426/98, 103, 534

[56] References Cited

U.S. PATENT DOCUMENTS

| | | | |
|---|---|---|---|
| 2,913,342 | 11/1959 | Cameron | 426/98 |
| 3,764,346 | 10/1973 | Noznick et al. | 426/96 X |
| 3,792,178 | 2/1974 | Noznick et al. | 426/96 |
| 3,895,105 | 7/1975 | Colten et al. | 426/306 |
| 3,949,094 | 4/1976 | Johnson et al. | 426/99 |
| 3,971,852 | 7/1976 | Brenner et al. | 426/103 |
| 3,985,913 | 10/1976 | Johnson et la. | 426/650 |
| 4,343,823 | 8/1982 | Todd, Jr. et al. | 426/250 |
| 4,883,680 | 11/1989 | Byrne | 426/534 |
| 4,919,941 | 4/1990 | Zibell | 426/5 |
| 4,925,678 | 5/1990 | Ranney | 424/493 |
| 4,963,367 | 10/1990 | Ecanow | 424/485 |
| 5,002,785 | 3/1991 | Lew | 426/303 |
| 5,015,483 | 5/1991 | Haynes et al. | 426/73 |
| 5,064,669 | 11/1991 | Tan et al. | 426/307 |
| 5,098,606 | 3/1992 | Nakajima et al. | 264/4.1 X |
| 5,137,726 | 8/1992 | Ogawa et al. | 424/408 X |

*Primary Examiner*—Richard D. Lovering
*Attorney, Agent, or Firm*—Fay, Sharpe, Beall, Fagan, Minnich & McKee

[57] ABSTRACT

In this invention, the purpose is to provide a shelf-stable spray-dried powder embodying a desired organic oil, such as a flavorant, for example. First, hydroxylated lecithin is subject to a high-energy power input, such as by vigorous stirring or microfluidization or sonication. To make a uniform mix, the resultant product is mixed with a poloxamer surfactant, water, and the desired organic oil, whether it be a flavoring, insect repellent, paint base or other organic oil. This is then subjected to energization input again, such as by microfluidization or sonication. Following this, bulking agents are added and the mixture is spray-dried. This invention shows the novel improvement of spray-dried material of the oil, lecithin, and surfactant to produce an extended shelf-life with little escape of organic oil ingredient.

6 Claims, No Drawings

ORGANIC OIL SPRAY-DRYING TECHNIQUES

DEFINITIONS

Organic oils: volatile or non-volatile water-insoluble organic compounds or mixtures of same used in food stuffs, consumer products, such as perfume and other fragrances, and skin care and skin use products such as insect repellents.

Surfactant: one that is capable of bridging and binding oil to hydroxylated lecithin. Poloxamer surfactants as those marketed by BASF Wyandotte Corporation under the trademark "PLURONIC" are suitable. One such is a commercially available block copolymer surfactant from BASF identified as "Pluronic F-127".

Nanodispersion: dispersion of one liquid in a second immiscible liquid, such that: (1) the average particle diameter of the dispersed liquid is in the range between 10 and 200 nanometers, and (2) the dispersion is stable for months at temperatures between 4 and 40° C.

FIELD OF THE INVENTION:

Water nanodispersion chemistry.

BRIEF DESCRIPTION OF THE INVENTION

This invention provides a method of preparing spray-dried formulations of organic oils such that the products are protected from loss by evaporation and from damage by oxidation, giving prolonged shelf-life to the product. This is accomplished by encapsulating the organic oil prior to spray-drying in a nanodispersion with a unique combination of edible surfactants. The invention has applicability in the food, cosmetic, and consumer products industries, among others.

BACKGROUND OF THE INVENTION

The most pertinent prior art is the industrial practice of drying emulsions of organic oils, normally referred to as flavorants, to prepare so-called instant beverages and for use in candy and medicines.

From a study of the literature and problems of spray-drying fragrances and flavorants as now practiced in the industry, it is understood that the standard for organic oils is that the obtainable limit of the oil concentration is 8 percent by weight when emulsified in water, and containing starches, malto-dextrins and/or gum arabic. Also, a long felt problem is that such emulsions lose a substantial proportion of their oils during storage after spray-drying.

It is an object of this invention to capture organic oils in a spray-dried form that will hold shelf-life with essentially no loss of the volatile organic components during or after spray-drying.

It is a further object of the invention to substantially decrease oxidation of fragile organic oil flavorants during spray-drying and storage.

Yet another object of this invention is to increase the proportion of organic oils in spray-dried materials above the industry standard.

DESCRIPTION OF THE PREFERRED EMBODIMENT

The invention will now be illustrated by a specific example in order that those skilled in this technology may better understand the practice of the invention. The invention is, of course, not limited to this specific example but includes all the features and advantages described above.

The detailed description hereafter will instruct in relating materials and methods for optimum usefulness for a given end product.

The description below allows for ranges of material and condition. The basic invention employs hydroxylated lecithin and surfactant to change the characteristics of the organic flavor oil. The oil, when prepared as described below will be uniformally dispersed in water without being emulsified, and as such displays remarkable new properties.

These preface remarks direct attention to the problem of the prior art, and the superior performance of the disclosure herein.

The difference between the prior art and this invention lies in the use of hydroxylated lecithin, and the anchoring of the oil to the hydroxylated lecithin by a surfactant capable of bridging and binding oil to hydroxylated lecithin.

To illustrate and teach this invention, orange oil was selected as the organic oil to give the most difficult challenge. Orange oil is not one compound, but a blend of many water-insoluble flavor components with a spectrum of volatilities and solubilities.

Because raw materials are obtained in various concentrations, a set of stock solutions was prepared from which known quantities of substance may be drawn. The procedure employed for these test materials was to prepare a 20 percent stock by weight of the hydroxylated lecithin in water, followed by microfluidization. To this stock was added the orange oil, the F-127 (also from a 20 percent stock in water) and the amount of additional water; this mixture is microfluidized.

As a control standard to test the theory of the invention, a control mix, designated "Preparation A", of 8 percent (all percents by weight) orange oil was microfluidized in water. After the oil and water mixture was microfluidized, an average particle diameter of $277\pm85$ nanometers was measured. Thereafter, 15 percent of malto-dextrin and 15 percent of gum arabic were added as bulking agents.

This control standard was spray-dried. During the spray-drying it was clear from the aroma that a substantial portion of the orange oil was volatilized and lost into the room air. This loss was quantitated for one component of the mixture by comparison of flavorant level before and after spray-drying- The spray-dried material also had a strong orange oil aroma, indicative of continued loss of flavorant subsequent to spray-drying.

A second and third mix according to this invention were prepared and tested. The second preparation, labeled "Preparation B", contained 8 percent orange oil, 2 percent hydroxylated lecithin, and 2.5 percent F-127 and water to yield 100%.

The third, labeled "Preparation C", contained 10 Percent orange oil, 2.5 percent hydroxylated lecithin, and 3.125 percent F-127 surfactant with water to yield 100%.

At this point, bulking agents as for "Preparation A" were added to both "Preparation B and C".

"Preparation B" was spray-dried and was essentially free from release of orange aroma during the spray-drying procedure, indicating that the orange oil had been successfully trapped in the material during spray-drying. "Preparation C", with 10% orange oil, was very viscous and would not easily pass through the very small apertures in the Brinkmann laboratory spray-dryer. However, the appearance and odor testing of the small amount of "Preparation C" which was successfully spray-dried, led to the conclusion that the same results that were measured for Preparation B would exist.

Loss of volatile orange oil components during spray-drying was evaluated by extracting portions of the mixtures before spray-drying with chloroform and determining the amount of a prominently-absorbing (at 330 nanometers) orange oil component in the extract by ultraviolet spectroscopy. For comparison, spray-dried materials from those same mixtures were resuspended in distilled water at a concentration designed to reconstitute the original mixture (based on the weight of solids) and then extracted and assayed in the same manner. The data of Table 1 confirm that there was a substantial ($\geq 34\%$) loss of the component of the orange oil which absorbs at 330 nanometers during the spray-drying process for "Preparation A". In contrast, there was an apparent gain of 13% in this component in "Preparation B". It is probable that this apparent gain with "Preparation B" was entirely due to loss of water from gum arabic during the spray-drying process, and that the same loss occurred during spray-drying of "Preparation A". If so, then the actual loss of 330 nanometers absorbing material in the spray-drying step for "Preparation A" was even greater than the 34.1% shown in the table.

TABLE 1

Loss of Orange Oil During Spray-drying

| Parameter | Prep A | Prep B |
|---|---|---|
| $A_{330}$/mg* solids before spray-drying | .152 | .132 |
| $A_{330}$/mg* solids after spray-drying | .100 | .149 |
| Percent change during spray-drying | −34.1 | +13.0 |

*$A_{330}$ is absorptivity at 330 nanometers in a spectrophotometer.

It was also found that spray-dried "Preparation B" reconstituted to a stable nanodispersion with water, while spray-dried "Preparation A" did not.

The spray-dried preparations A and B were tested for the retention of orange oil components as a measure of shelf-life. The spray-dried materials were normally kept in air-tight containers. Human testers were employed over a period of two months to determine the presence or absence of orange aroma in these materials maintained in this way. During this time period the testers confirmed that "Preparation A" had a strong orange aroma whereas The conclusion from these test procedures was that the orange oil flavorant was not stably incorporated in spray-dried "Preparation A". Furthermore, since the spray-dried "Preparation B" had distinct orange oil aroma only after reconstitution in water, it was concluded that the flavorant must also have been present in the spray-dried materials of "Preparation B", but in some entrapped form that minimized volatilization.

The evidence leads to the conclusion that "B and C" have longer shelf-lives than "A". The relative shelf-lives "Preparation A and B" were also quantitated as shown below. Evaluation was done by investigating how much of the same 330 nanometers absorbing component of the flavorant was lost when the spray-dried materials were exposed uncovered in the fume hood with the fan on for 32 days. After that exposure time the exposed materials were reconstituted with water as above, and the remaining orange oil was extracted from each and quantitated by spectroscopy.

TABLE 2

Loss of orange oil During Air-exposure

| Parameter | Prep A | Prep B |
|---|---|---|
| Net wt before air-exposure (mg) | 467 | 452 |
| Net wt after air-exposure (mg) | 495 | 474 |
| % Increment in net wt | 6.0 | 5.0 |
| Total $A_{330}$ before spray-drying* | 75.0 | 62.6 |
| Total $A_{330}$ after air-exposure | 32.3 | 58.1 |
| % Loss during air-exposure | 30.7 | 13.8 |
| % Loss during air-exposure + spray-drying | 56.9 | 7.2 |

*Calculated by multiplying $A_{330}$/mg solids before spray-drying by net wt after air-exposure, assuming that the weight loss during spray-drying from $H_2O$ in gum arabic or malto-dextrins = net weight gain during air-exposure.

Examples of other applications for the spray-drying technique of the invention:

1. Instant orange juice, lemonade, lime-aid, other fruit juices—no loss of flavor during storage.
2. Room air fresheners which consumer activates by adding water—indefinite shelf-life before activation.
3. Dried paint solids; activated by water addition and shaking at paint store—not ship water.
4. Personal fragrances (perfumes) released by perspiration.
5. Flavor additives without alcohol or loss by evaporation for baking and cooking, added to other ingredients by dry measure—saves on shipping, organics in the environment, spilling, and shelf-life.
6. Dried fertilizers without odor or loss of nitrogenous components.
7. Dried pesticides and herbicides (e.g. atrazine), activated by dispersion in water—no spills, not ship water, reduced breakdown prior to dispersion in soil by rain.

Example of the Preferred Embodiment

The invention will now be illustrated by a specific example of the preferred procedure in order that those skilled in this technology may better understand the practice of the invention. The invention is, of course, not limited to this specific example, but includes all the features and advantages described above.

1. As received from the manufacturer, hydroxylated lecithin is very viscous. Therefore, step one is to obtain a stock of 20% hydroxylated lecithin in water. This may be accomplished by vigorous stirring, but is best done by polytroning. This mix is a unique lecithin structure classed as a surfactant.

2. The next step, as part of this invention, may be done in one of two electable alternatives.

(A) Using a uniform dispersion of hydroxylated lecithin as specified above, the product of step one is microfluidized to produce a dispersed hydroxylated lecithin to which is added the appropriate amounts of a stock of F-127, water and organic oil. The mixture is microfluidized again. The microfluidized steps produce at least some liposomal structure.

(B) As an alternative, the 20% hydroxylated lecithin, the F-127 and the organic oil are mixed and then microfluidized.

Finally, the product of either alternate 1) or 2) is bulked to a consistency that will flow through a spray dryer.

What is claimed is:

1. The method comprising microfluidizing hydroxylated lecithin and water, adding organic oil and surfactant a "PLURONIC" non-ionic poloxamer and re-microfluidizing, thereafter adding bulking agents and spray-drying the mixture, whereby a shelf-stable powder is obtained having little oil escape over an extended period of time.

2. The method of making a spray-dried mixture of organic oil and bulking agents having a stable shelf-life for an extended time, comprising:
   (1) microfluidizing hydroxylated lecithin and water to obtain an average particle diameter of $\leq 140$ nanometers;
   (2) thereafter adding organic oil and a "PLURONIC" non-ionic poloxamer surfactant to a "PLURONIC" non-ionic poloxamer product of step (1);
   (3) microfluidizing the mix of (2);
   (4) adding bulking agents to the product of step (3); and
   (5) finally spray-drying the product of step (4).

3. The method of claim 2, wherein the average particle size is in the range of 5–140 nanometers.

4. The method of claim 2, wherein the organic oil is in a range up to 37% of the resultant product.

5. The method of claim 2, wherein the hydroxylated lecithin is in a range up to 10% of the resultant product.

6. The method of making a spray-dried mixture of organic oil and bulking agents having a stable shelf-life for an extended time, comprising:
   (1) preparing a uniform dispersion of hydroxylated lecithin and water;
   (2) adding organic oil and a "PLURONIC" non-ionic poloxamer surfactant to the dispersion of step (1);
   (3) microfluidizing the mix of step (2);
   (4) adding bulking agents to the product of step (3); and
   (5) finally spray-drying the product of step (4).

* * * * *